(12) United States Patent
Pelletier et al.

(10) Patent No.: US 8,268,805 B2
(45) Date of Patent: Sep. 18, 2012

(54) USE OF CERAMIDES FOR DEPIGMENTING THE SKIN

(75) Inventors: Pascale Pelletier, Antony (FR); Catherine Marion, Antony (FR)

(73) Assignee: L'Oreal, Paris (FR)

( * ) Notice: Subject to any disclaimer, the term of this patent is extended or adjusted under 35 U.S.C. 154(b) by 1037 days.

(21) Appl. No.: 12/097,408

(22) PCT Filed: Dec. 15, 2006

(86) PCT No.: PCT/FR2006/051370
§ 371 (c)(1),
(2), (4) Date: Aug. 21, 2008

(87) PCT Pub. No.: WO2007/071875
PCT Pub. Date: Jun. 28, 2007

(65) Prior Publication Data
US 2009/0192124 A1    Jul. 30, 2009

Related U.S. Application Data

(60) Provisional application No. 60/752,007, filed on Dec. 21, 2005.

(30) Foreign Application Priority Data

Dec. 16, 2005    (FR) ...................... 05 53911

(51) Int. Cl.
*A61K 31/60* (2006.01)
(52) U.S. Cl. ...................... 514/162; 514/669
(58) Field of Classification Search .............. 514/162
See application file for complete search history.

(56) References Cited

U.S. PATENT DOCUMENTS

| | | | | |
|---|---|---|---|---|
| 5,589,178 | A * | 12/1996 | Aubert et al. | 424/401 |
| 6,348,204 | B1 * | 2/2002 | Touzan | 424/401 |
| 2005/0032751 | A1 * | 2/2005 | Wang et al. | 514/114 |

FOREIGN PATENT DOCUMENTS

| | | |
|---|---|---|
| EP | 0 500 437 | 8/1992 |
| EP | 0 647 617 | 4/1995 |
| EP | 0 662 319 | 7/1995 |
| EP | 0 919 226 | 6/1999 |
| EP | 1 552 816 | 7/2005 |
| FR | 2 732 594 | 10/1996 |
| JP | 2005 002021 | 1/2005 |
| WO | 2004 045573 | 6/2004 |
| WO | 2005 063688 | 7/2005 |

OTHER PUBLICATIONS

Wikipedia (http://en.wikipedia.org/ wiki/Human_skin_color).*
Masanori et al (JP2005-002021 machine language translation).*
Goldschmidt: "Ceramide IIIA", The Art of Formulating, pp. 1-4, XP002397987, (2004).
Dong-Seok, K. et al., Delayed ERK Activation by Ceramide Reduces Melanin Synthesis in Human Melanocytes, Cellular Signalling, vol. 14, pp. 779-785, XP002397818, (2002).

* cited by examiner

*Primary Examiner* — Jake M. Vu
(74) *Attorney, Agent, or Firm* — Oblon, Spivak, McClelland, Maier & Neustadt, L.L.P.

(57) ABSTRACT

The invention relates to the use, as agent for depigmenting and/or whitening the skin, in particular for eliminating pigmentary spots and/or senescence spots, and/or as anti-browning agents, of a compound of formula (I):

$$R_1\text{—CHOH—CH(NH—COR}_2)(CH_2OH) \qquad (I)$$

in which $R_1$ denotes a $C_{11}$ to $C_{21}$ alkyl radical, and $R_2$ denotes a linear, optionally hydroxylated $C_{11}$-$C_{19}$ hydrocarbon-based radical, with the hydroxyl group being in the alpha-position with respect to the carbonyl, which may comprise one or more ethylenic unsaturations, in particular one or two ethylenic unsaturations.

The invention also relates to a cosmetic process for depigmenting and/or lightening skin exhibiting pigmentation spots, comprising the application to the skin of a composition comprising, in a physiologically acceptable medium, a compound of formula (I).

10 Claims, No Drawings

USE OF CERAMIDES FOR DEPIGMENTING THE SKIN

CROSS-REFERENCE TO RELATED APPLICATIONS

This application is a National Stage of PCT/FR06/51370 filed Dec. 15, 2006, which is a non-provisional of 60/752,007 filed on Dec. 21, 2005. This application is based upon and claims the benefit of priority from French Patent Application No. 0553911 filed Dec. 16, 2005.

BACKGROUND OF THE INVENTION

The present invention relates to the use of specific ceramides as skin-depigmenting agent, and also to a process for depigmenting the skin.

Human skin colour depends on various factors, and in particular on the seasons of the year, on race and on gender; it is mainly determined by the nature and the concentration of melanin produced by melanocytes. Melanocytes are specialized cells which synthesize melanin by means of specific organelles, melanosomes. In addition, at various times in their life, certain individuals experience the appearance of dark and/or coloured spots on the skin and more especially on the hands, which give the skin a heterogeneity. These spots are also due to a high concentration of melanin in the keratinocytes located at the skin surface.

The use of harmless topical depigmenting substances that are very effective is most particularly desired with a view to treating regional hyperpigmentations due to melanocyte hyperactivity, such as idiopathic melasmas, occurring during pregnancy ("pregnancy mask" or chloasma) or oestroprogestatin contraception, localized hyperpigmentations due to benign melanocyte hyperactivity and proliferation, such as senile pigmentation spots referred to actinic lentigo, accidental hyperpigmentations, possibly due to post-lesional cicatrization or photosensitization, and also certain forms of leukoderma, such as vitiligo. For the latter (the cicatrizations possibly resulting in a scar that gives the skin a whiter appearance), since it is not possible to repigment the lesioned skin, the process is finished off by depigmenting the areas of residual normal skin so as to give the skin as a whole a homogeneous white tint.

The mechanism of formation of skin pigmentation, i.e. of the formation of melanin, is particularly complex and involves, schematically, the following main steps:
Tyrosine→Dopa→Dopaquinone→Dopachrome→Melanin Tyrosinase (monophenol dihydroxyl phenylalanine:oxygen oxidoreductase EC 1.14.18.1) is the essential enzyme involved in this series of reactions. It catalyses in particular the reaction for conversion of tyrosine to Dopa (dihydroxyphenylalanine) by virtue of its hydroxylase activity and the reaction for conversion of Dopa to dopaquinone by virtue of its oxidase activity. This tyrosinase acts only when it is in the maturation state under the action of certain biological factors.

A substance is recognized being a depigmenting substance if it acts directly on the vitality of epidermal melanocytes where melanogenesis takes place, and/or if it interferes with one of the steps of melanin biosynthesis, either by inhibiting one of the enzymes involved in melanogenesis, or by intercalating as a structural analogue of one of the chemical compounds of the melanin synthesis chain, which chain can then be blocked, and thus ensuring depigmentation.

The substances most commonly used as depigmenting agents are, more particularly, hydroquinone and its derivatives, in particular its ethers such as hydroquinone monomethyl ether and hydroquinone monoethyl ether. Although they have a certain level of effectiveness, these compounds are, unfortunately, not free of side effects on account of the toxicity that they entail, which may make them complicated, or even dangerous, to use. This toxicity arises from the fact that they intervene in fundamental mechanisms of melanogenesis by killing cells which then run the risk of disturbing their biological environment and which consequently oblige the skin to eliminate them by producing toxins.

Thus, hydroquinone is a compound which is particularly irritant and cytotoxic to melanocytes, and whose total or partial replacement has been envisaged by many authors.

Substances have thus been sought which do not intervene in the mechanism of melanogenesis but which act upstream on tyrosinase by preventing its activation and are, as a result, much less toxic. Kojic acid is commonly used as an inhibitor of tyrosinase activation, said kojic acid complexing the copper present in the active site of this enzyme. Unfortunately, this compound is unstable in solution, thereby somewhat complicating the manufacture of the composition.

There remains the need for a new agent for whitening human skin which has an action that is as effective as the known agents, but which does not have their drawbacks, i.e. which is nonirritant, nontoxic and/or nonallergenic for the skin.

BRIEF SUMMARY OF THE INVENTION

In this regard, the applicant has, surprisingly and unexpectedly, discovered that certain ceramide compounds exhibit a good depigmenting activity.

More specifically, a subject of the invention is therefore the use, as agent for depigmenting and/or whitening the skin, in particular for eliminating pigmentary spots and/or senescence spots, and/or as anti-browning agents,
of a compound of formula (I) below:

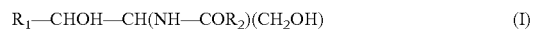

$$R_1\text{—CHOH—CH(NH—COR}_2\text{)(CH}_2\text{OH)} \tag{I}$$

in which $R_1$ denotes a $C_{11}$ to $C_{21}$ alkyl radical, and $R_2$ denotes a linear, optionally hydroxylated $C_{11}$-$C_{19}$ hydrocarbon-based radical, with the hydroxyl group being in the alpha-position with respect to the carbonyl, which can comprise one or more ethylenic unsaturations, in particular one or two ethylenic unsaturations.

A subject of the invention is also a cosmetic process for depigmenting and/or lightening skin exhibiting pigmentation spots, comprising the application to the skin of a composition comprising, in a physiologically acceptable medium, at least one compound of formula (I) as described above. The process is suitable in particular for eliminating brownish pigmentary spots and/or senescence spots, and/or for lightening browned skin.

A subject of the invention is also the use of a compound of formula (I) as described above, for the manufacture of a dermatological composition for use in depigmenting and/or whitening the skin.

DETAILED DESCRIPTION OF THE INVENTION

The compounds of formula (I) according to the invention make it possible to effectively depigment and/or lighten human skin. They are in particular intended to be applied to the skin of individuals exhibiting brownish pigmentation spots or senescence spots, or to the skin of individuals wishing to combat the appearance of a brownish colour originating from melanogenesis, for example following exposure to ultraviolet radiation.

For the compounds of formula (I), $R_1$ preferably denotes a $C_{13}$-$C_{19}$ hydrocarbon-based radical; $R_2$ denotes a linear, optionally hydroxylated $C_{13}$-$C_{19}$ hydrocarbon-based radical which can comprise one or more ethylenic unsaturations.

Preferably, $R_1$ denotes a $C_{13}$-$C_{17}$ hydrocarbon-based radical; $R_2$ denotes a linear, optionally hydroxylated $C_{13}$-$C_{19}$ hydrocarbon-based radical which can comprise one or more ethylenic unsaturations.

Advantageously, $R_1$ denotes a $C_{13}$-$C_{17}$ hydrocarbon-based radical; $R_2$ denotes either a linear $C_{13}$-$C_{19}$ hydrocarbon-based radical which can comprise one or more ethylenic unsaturations, or a saturated, linear, hydroxylated $C_{13}$-$C_{19}$ hydrocarbon-based radical, the hydroxyl group being in the alpha-position with respect to the carbonyl.

As compounds of formula (I) that are particularly preferred, use may be made of N-oleyldihydrosphingosine and N-2-hydroxypalmitoyldihydrosphingosine.

The compounds of formula (I) are known from the prior art, in particular in applications EP-A-500437 and EP-A-647617.

The article "Delayed ERK activation by ceramide reduces melanin synthesis in human melanocytes" by Dong-Seok Kim et al., Cellular Signaling, 14 (2002), p. 779-785, describes the fact that N-acetyl-D-erythrosphingosine has an effect on the tyrosinase activity of the melanocytes of human skin, unlike sphingosine-1-phosphate, which has no effect.

The company Cosmoferm sells N-linoleoylphytosphingosine under the name Ceramide IIIA® and which is known to have a depigmenting action on the skin.

In the context of the present invention, the term "alkyl" means a saturated or unsaturated, hydrocarbon-based chain.

The composition used according to the invention comprises, in a physiologically acceptable medium, at least one ceramide corresponding to formula (I) as defined above.

In particular, the composition is suitable for topical application to the skin. The physiologically acceptable medium will preferably be a cosmetically or dermatologically acceptable medium, i.e. having no unpleasant smell, colour or appearance, and which does not generate any stinging, tautness or redness unacceptable to the user.

The term "physiologically acceptable medium" is understood to mean a medium compatible with the keratin materials of human beings, such as the skin, the mucous membranes, the nails, the scalp and/or the hair.

The composition according to the invention may be for cosmetic or pharmaceutical, particularly dermatological, application. Preferably, the composition according to the invention is for cosmetic application.

The ceramide of formula (I) may be present in the composition used according to the invention in a content ranging from 0.001% to 10% by weight, preferably from 0.01% to 5% by weight, in particular from 0.1% to 2% by weight, relative to the total weight of the composition.

The composition may then comprise any of the constituents normally used in the application envisaged.

Mention may be in particular be made of water, solvents, oils of mineral, animal and/or plant origin, waxes, pigments, fillers, surfactants, cosmetic or dermatological active agents, UV screening agents, polymers, gelling agents and preservatives.

Of course, those skilled in the art will take care to select this or these optional additional compound(s), and/or the amount thereof, in such a way that the advantageous properties of the compounds according to the invention are not, or are not substantially, impaired by the addition envisaged.

The composition according to the invention may be in any of the galenical forms normally used in the cosmetics and dermatological fields; it may in particular be in the form of an optionally gelled, aqueous or aqueous-alcoholic solution, of an optionally two-phase dispersion of the lotion type, of an oil-in-water or water-in-oil or multiple emulsion, of an aqueous gel, of a dispersion of oil in an aqueous phase by means of spherules, it being possible for these spherules to be polymeric nanoparticles such as nanospheres and nanocapsules, or better still lipid vesicles of ionic and/or nonionic type.

When the composition is an emulsion, the proportion of the fatty phase can range from 5% to 80% by weight, and preferably from 5% to 50% by weight, relative to the total weight of the composition. The oils, the emulsifiers and the optional coemulsifiers used in the composition in emulsion form are chosen from those conventionally used in the field under consideration. The emulsifier and the coemulsifier are present in the composition in a proportion that can range from 0.3% to 30% by weight, and preferably from 0.5% to 20% by weight, relative to the total weight of the composition.

This composition may be more or less fluid and may have the appearance of a white or coloured cream, an ointment, a milk, a lotion, a serum, a paste or a foam. It may optionally be applied to the skin in the form of an aerosol. It may also be in the form of a solid, and for example in the form of a stick.

In an advantageous aspect of the invention, the compositions used may also comprise at least one desquamating agent and/or at least one calmative and/or at least one organic photoprotective agent and/or at least one inorganic photoprotective agent.

The term "desquamating agent" is intended to mean any compound capable of acting:

either directly on desquamation by promoting exfoliation, examples being β-hydroxy acids, in particular salicylic acid and its derivatives (including 5-n-octanoylsalicylic acid); α-hydroxy acids, such as glycolic acid, citric acid, lactic acid, tartaric acid, maleic acid or mandelic acid; urea; gentisic acid; oligofucoses; cinnamic acid; extract of Sophora japonica; resveratrol;

or on the enzymes involved in desquamation or degradation of corneodesmosomes, glycosidases, stratum corneum chymotropic enzyme (SCCE), or even other proteases (trypsin, chymotrypsin-like). Mention may be made of agents that chelate mineral salts: EDTA; N-acyl-N,N',N'-ethylenediaminetriacetic acid; aminosulphonic compounds and, in particular, (N-2-hydroxyethylpiperazine-N-2-ethane)sulphonic acid (HEPES) (also known as 4-(2-hydroxyethyl)piperazine-1-ethanesulphonic acid); derivatives of 2-oxothioazolidine-4-carboxylic acid (procysteine); derivatives of alpha-amino acids of glycine type (as described in EP-0 852 949, and also the sodium methyl glycine diacetate sold by BASF under the trade name Trilon M); honey; sugar derivatives such as O-octanoyl-6-D-maltose and N-acetylglucosamine.

The desquamating agent may be present in the composition for the use according to the invention in a content ranging from 0.1% to 10% by weight, relative to the total weight of the composition, preferably ranging from 0.1% to 5% by weight, and preferentially ranging from 0.5% to 2% by weight.

The salicylic acid derivatives mentioned above may be chosen from the compounds of formula (II) below:

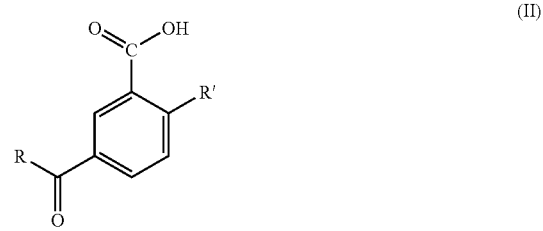

in which:

the radical R denotes a linear, branched or cyclic, saturated aliphatic chain containing from 2 to 22 carbon atoms; an unsaturated chain containing from 2 to 22 carbon atoms containing one or more double bonds that may be conjugated; an aromatic ring linked to the carbonyl radical directly or by means of saturated or unsaturated aliphatic chains containing from 2 to 7 carbon atoms; it being possible for said groups to be substituted with one or more substituents, which may be identical or different, chosen from (a) halogen atoms, (b) a trifluoromethyl group, (c) hydroxyl groups in free form or in a form esterified with an acid containing from 1 to 6 carbon atoms, or (d) a carboxyl function in free form or in a form esterified with a lower alcohol containing from 1 to 6 carbon atoms;

R' is an hydroxyl group;

and also the salts thereof derived from an inorganic or organic base.

Preferably, the radical R denotes a linear, branched or cyclic, saturated aliphatic chain containing from 3 to 11 carbon atoms; an unsaturated chain containing from 3 to 17 carbon atoms and comprising one or more double bonds which may or may not be conjugated; it being possible for said hydrocarbon-based chains to be substituted with one or more substituents, which may be identical or different, chosen from (a) halogen atoms, (b) a trifluoromethyl group, (c) hydroxyl groups in free form or in a form esterified with an acid containing from 1 to 6 carbon atoms, or (d) a carboxyl function in free form or in a form esterified with a lower alcohol containing from 1 to 6 carbon atoms;

and also the salts thereof obtained by salification with an inorganic or organic base.

The compounds that are more particularly preferred are those in which the radical R is a $C_3$-$C_{11}$ alkyl group.

Among the compounds of formula (I) that are particularly preferred, mention may be made of: 5-n-octanoylsalicylic acid (or capryloylsalicylic acid); 5-n-decanoylsalicyclic acid; 5-n-dodecanoyl-salicyclic acid; 5-n-heptyloxysalicyclic acid, and the corresponding salts thereof.

5-n-Octanoylsalicylic acid will more particularly be used.

The salts of the compounds of formula (II) can be obtained by salification with an inorganic or organic base. By way of example of an inorganic base, mention may be made of alkali metal hydroxides or alkaline earth metal hydroxides, such as sodium hydroxide or potassium hydroxide, or aqueous ammonia.

Among the organic bases, mention may be made of amines and alkanolamines. Quaternary salts such as those described in patent FR 2 607 498 are particularly advantageous.

The compounds of formula (II) that can be used according to the invention are described in U.S. Pat. No. 6,159,479 and U.S. Pat. No. 5,558,871, FR 2,581,542, FR 2,607,498, U.S. Pat. No. 4,767,750, EP 378,936, U.S. Pat. No. 5,267,407, U.S. Pat. No. 5,667,798, U.S. Pat. No. 5,580,549, and EP-A-570,230.

According to a preferred embodiment of the invention, the composition used according to the invention contains a ceramide of formula (I) and a compound of formula (II).

A composition containing N-oleoyldihydrosphingosine and 5-n-octanoylsalicylic acid is advantageously used. Such a composition has a good skin-depigmenting performance level, as shown by comparative example 4 described hereinafter.

A composition comprising N-2-hydroxypalmitoyldihydro-sphingosine and 5-n-octanoylsalicylic acid may also be used.

The aminosulphonic compounds mentioned above can be chosen from the compounds of formula (III) below:

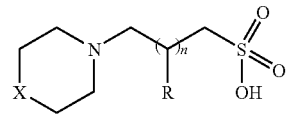

(III)

in which:

R denotes a hydrogen atom or an —OH group,

X denotes a N—CH$_2$CH$_2$OH group, n is equal to 0 or 1.

As compound of formula (III), mention may be made of:
(N-2-hydroxyethylpiperazine-N-2-ethane)sulphonic acid (HEPES);
4-(2-hydroxyethyl)piperazine-1-(2-hydroxypropane-sulphonic) acid;
4-(2-hydroxyethyl)piperazine-1-propanesulphonic acid.

(N-2-Hydroxyethylpiperazine-N-2-ethane)sulphonic acid (HEPES) is in particular used.

According to a preferred embodiment of the invention, the composition used according to the invention contains a ceramide of formula (I) and a compound of formula (III).

A composition containing N-oleoyldihydrosphingosine and (N-2-hydroxyethylpiperazine-N-2-ethane)sulphonic acid (HEPES) is advantageously used.

A composition comprising N-2-hydroxypalmitoyldihydro-sphingosine and (N-2-hydroxyethylpiperazine-N-2-ethane)sulphonic acid (HEPES) can also be used.

As calmatives that can be used in the composition used according to the invention, mention may be made of: pentacyclic triterpenes and extracts of plants (for example: *Glycyrrhiza glabra*) containing them, such as β-glycyrrhetinic acid and salts thereof and/or derivatives thereof (glycyrrhetinic acid monoglucuronide, stearyl glycyrrhetinate, 3-stearoyloxyglycyrrhetic acid), ursolic acid and salts thereof, oleanolic acid and salts thereof, betulinic acid and salts thereof, an extract of *Paeonia suffruticosa* and/or lactiflora, salicylic acid salts, and in particular zinc salicylate, the phycosaccharides from the company Codif, an extract of *Laminaria saccharina*, canola oil, bisabolol and extracts of camomile, allantoin, Sepivital EPC (phosphoric diester of vitamin E and C) from Seppic, omega 3-unsaturated oils such as rose muscat oil, blackcurrant oil, ecchium oil, fish oil, extracts of plankton, caprylolylglycine, Seppicalm VG (sodium palmitoylproline and *Nymphea alba*) from Seppic, an extract of Pygeum, an extract of *Boswellia serrata*, an extract of *Centipeda cunninghami*, an extract of *Helianthus annuus*, an extract of *Linum usitatissimum*, tocotrienols, extracts of *Cola nitida*, piperonal, an extract of clove, an extract of *Epilobium angustifolium*, *Aloe vera*, an extract of *Bacopa monierea*, phytosterols, cortisone, hydrocortisone, indomethacin and betamethasone.

The organic photoprotective agents are in particular chosen from anthranilates; cinnamic derivatives; dibenzoylmethane derivatives; salicylic derivatives, camphor derivatives; triazine derivatives such as those described in patent applications U.S. Pat. No. 4,367,390, EP863145, EP517104, EP570838, EP796851, EP775698, EP878469, EP933376, EP507691, EP507692, EP790243, EP944624; benzophenone derivatives; β,β-diphenylacrylate derivatives; benzotriazole derivatives; benzalmalonate derivatives; benzimidazole derivatives; imidazolines; the bisbenzoazolyl derivatives as described in patents EP669323 and U.S. Pat. No. 2,463,264; p-aminobenzoic acid (PABA) derivatives; the methylenebis(hydroxyphenylbenzo-triazole) derivatives as described in applications U.S. Pat. No. 5,237,071, U.S. Pat. No. 5,166,355, GB 2303549, DE 197 26 184 and EP 893119; screening polymers and screening silicones such as those described in particular in application WO-93/04665; dimers derived from α-alkylstyrene such as those described in patent application DE 19855649.

The inorganic photoprotective agents are chosen from coated or uncoated metal oxide pigments or alternatively nanopigments (mean size of the primary particles: generally between 5 nm and 100 nm, preferably between 10 nm and 50 nm), for instance nanopigments of titanium oxide (amorphous or crystallized in rutile and/or anatase form), iron oxide, zinc oxide, zirconium oxide or cerium oxide nanopigments, which are all uv-photoprotective agents that are well known per se. Conventional coating agents are, moreover, alumina and/or aluminium stearate. Such coated or uncoated metal oxide nanopigments are in particular described in patent applications EP518772 and EP518773.

The photoprotective agents are generally present in the composition according to the invention in proportions ranging from 0.1% to 20% by weight, relative to the total weight of the composition, and preferably ranging from 0.2% to 15% by weight, relative to the total weight of the composition.

The examples which follow illustrate the invention.

Example 1

Demonstration of the Activity on Melanogenesis

A biological test demonstrated the depigmenting activity of the following 2 compounds: N-oleoyldihydro-sphingosine and N-2-hydroxypalmitoyldihydrosphingosine.

The modulatory effect on melanogenesis of the compounds tested was measured according to the method described in patent FR-A-2734825, and also in the article by R. Schmidt, P. Krien and M. Regnier, Anal. Biochem., 235(2), 113-18, 1996. This test is carried out on a coculture of keratinocytes and melanocytes.

For the compound tested, the inhibitory activity on melanin synthesis was determined by estimating the ratio of thiouracil incorporation to leucine incorporation, related to 100% of the control (the control corresponds to the test carried out without compound to be tested). The IC50 values (concentration for which 50% of the melanin synthesis is inhibited) were determined.

The test was also carried out with arbutin and lucinol (2-butylbenzene-1,3-diol), which are known depigmenting compounds.

The results are given in the following table:

|  | IC50 (μM) |
|---|---|
| N-oleoyldihydrosphingosine | 0.1 |
| N-2-hydroxypalmitoyldihydrosphingosine | 0.1 |
| Arbutin | 209 |
| Lucinol | 2 |

The 2 compounds tested according to the invention are indeed effective in inhibiting melanogenesis.

Example 2

A depigmenting composition containing the following ingredients was prepared:

| | |
|---|---|
| Triethanolamine | 0.5 g |
| Sucrose stearate | |
| (Tegosoft ® PSE 141 G from Goldschmidt) | 3 g |
| Myristic acid | 0.03 g |
| N-2-hydroxypalmitoyldihydrosphingosine | 1 g |
| Palmitic acid | 0.44 g |
| Stearic acid | 0.53 g |
| Apricot kernel oil | 20 g |
| Methyl glucose sesquistearate | 1 g |
| (Glucate ® SS from Noveon) | |
| Preservatives | qs |
| Carbomer | 0.5 g |
| Water | qs 100 g |

The composition applied to skin exhibiting pigmentation spots makes it possible to fade out the spots after several applications.

Example 3

A depigmenting composition containing the following ingredients was prepared:

| | |
|---|---|
| Water | qs 100 g |
| Glycerol | 3 g |
| Preservatives | 0.1 g |
| Disodium salt of ethylenediaminetetraacetic acid | |
| Xanthan gum | 0.2 g |
| Polydimethylsiloxane | 3 g |
| (Fluid DC200 10 cst from Dow Corning) | |
| Preservative | 0.05 g |
| Hydrogenated isoparaffin (Parleam from NOF Corporation) | 3 g |
| White petroleum jelly | 1 g |
| Mixture of glyceryl monostearate and of polyethylene glycol stearate (100 EO) (Simulsol 165 from the company Seppic) | 1.4 g |
| Cetyl alcohol | 1 g |
| N-oleoyldihydrosphingosine | 0.01 g |
| Octyldodecanol | 1 g |
| Polysaccharide at 1% in water (Fucogel 1000 from the company Solabia) | 1 g |
| Acrylamide/sodium acrylamido-2-methyl-propanesulphonate copolymer as an inverse emulsion at 40% in isoparaffin/water (Sepigel 305 from Seppic) | 2.4 g |
| Sodium hyaluronate | 0.01 g |
| Water | 7 g |

The composition applied to skin exhibiting pigmentation spots makes it possible to fade out the spots after several applications.

Comparative Example 4

A composition 4a according to the invention containing the combination of N-oleoyldihydrosphingosine and 5-n-octanoylsalicylic acid, a composition 4b according to the invention containing N-oleoyldihydrosphingosine and a composition 4c which is not part of the invention, containing 5-n-octanoylsalicylic acid, were prepared.

These compositions comprised the following ingredients (contents as % by weight):

| | Example 4a | Example 4b | Example 4c |
|---|---|---|---|
| Disodium salt of ethylene-diaminetetraacetic acid | 0.15 | 0.15 | 0.15 |
| 5-n-Octanoylsalicylic acid | 2 | — | 2 |
| Triethanolamine | 0.9 | 0.5 | 0.8 |
| Cetyl alcohol | 0.4 | 0.4 | 0.4 |

-continued

|  | Example 4a | Example 4b | Example 4c |
|---|---|---|---|
| N-Oleoyldihydrosphingosine | 1 | 1 | — |
| Isopropyl N-lauroylsarcosinate | 10 | 10 | 10 |
| Preservatives | qs | qs | qs |
| Acrylic acid/stearyl methacrylate copolymer (Carbopol 1382 from NOVEON) | 0.5 | 0.5 | 0.5 |
| Acrylamide/sodium acrylamido-2-methylpropanesulphonate copolymer as an inverse emulsion at 40% (Simulgel 600 from SEPPIC) | 1 | 1 | 1 |
| Cyclohexasiloxane | 5 | 5 | 5 |
| Ethanol | 5 | 5 | 5 |
| Glycerol | 3 | 3 | 3 |
| Mixture of glyceryl stearate and PEG-100 stearate (ARLACEL ® 165 FL from Uniqema) | 0.3 | 0.3 | 0.3 |
| Water | qs 100 | qs 100 | qs 100 |

The depigmenting properties of these compositions were evaluated on a panel of 18 individuals with Asiatic skin. For each individual, the minimum erythemal dose (MED) was determined in a known manner.

Two zones 2.25 cm² in size (1.5 cm×1.5 cm) were determined on each forearm of an individual.

Using a colour chart having 52 hues corresponding to different skin colours and for which each lightness parameter C* and hue angle parameter h in the CIE 1976 calorimetric space is quantified, the hue on the colour chart which resembles the colour exhibited by each zone of the forearm is determined. The lightness C* of the colour thus evaluated is then noted.

Each zone is then exposed to UV/SSR radiation with a solar simulator lamp from Oriel. UV radiation corresponding to 2 minimum erythemal doses (MEDs) was first undergone, and then, after waiting for 2 days and according to the colour of the irradiated skin zone, a corresponding radiation of 1.75 to 2.5 MED was subsequently undergone. This operation was repeated once again 2 days later.

Seven days after the final UV irradiation carried out, the zones of the skin exhibit a pigmentation and the colour of each zone is again measured using the colour chart (this measurement is therefore carried out at To) and the corresponding lightness value C* (To) is determined.

The treatment of the zones of the forearms with the compositions to be tested is then commenced in order to evaluate their depigmenting action.

An amount of 9 μg of one of the compositions 4a, 4b, 4c was applied to 3 of the 4 total zones (therefore just one composition is applied to one zone) and the fourth zone is not treated.

The compositions are applied thus twice daily (morning and evening) for 6 weeks.

After treatment for 6 weeks (T6), the colour of each zone treated is again measured using the colour chart. The corresponding lightness value C* (T6) is thus determined and is compared with the lightness C* (To) measured at To before the application of the products.

The mean of the values obtained before and after treatment is calculated and compared with an Anova statistical test.

The following results were obtained:

|  | Ex 4c | Ex 4b | Ex 4a | Control zone (not treated) | Probability p: according to Anova test |
|---|---|---|---|---|---|
| Δ C* (T6 − T0) | −1.7 ± 1.2 | −1.8 ± 1.1 | −2.5 ± 1.1 | −0.7 ± 1.2 | <0.001 |

The results obtained are clearly significant since p<0.001.

The results obtained show that composition 4a containing the combination of N-oleoyldihydro-sphingosine and 5-n-octanoylsalicylic acid makes it possible to obtain a skin lightening result that is greater than those obtained with composition 4b containing N-oleoyldihydrosphingosine and with composition 4c containing 5-n-octanoylsalicylic acid. The lightening result obtained with composition 4b is also greater than that obtained with composition 4c.

The combination of N-oleoyldihydrosphingosine and 5-n-octanoylsalicyclic acid therefore has a better depigmenting activity.

Example 5

A skin depigmenting composition having the following composition is prepared (contents as % by weight):

|  | Example 5 |
|---|---|
| Disodium salt of ethylenediaminetetra-acetic acid | 0.15 |
| Triethanolamine | 0.9 |
| Cetyl alcohol | 0.4 |
| N-oleoyldihydrosphingosine | 1 |
| Isopropyl N-lauroylsarcosinate | 10 |
| Preservatives | qs |
| Acrylic acid/stearyl methacrylate copolymer (Carbopol 1382 from NOVEON) | 0.5 |
| Acrylamide/sodium acrylamido-2-methyl-propanesulfonate copolymer as an inverse emulsion at 40% (Simulgel 600 from SEPPIC) | 1 |
| Cyclohexasiloxane | 5 |
| (N-2-hydroxyethylpiperazine-N-2-ethane)sulphonic acid | 1 |
| Ethanol | 5 |
| Glycerol | 3 |
| Mixture of glyceryl stearate and PEG 100 stearate (ARLACEL ® 165 FL from Uniqema) | 0.3 |
| Water | qs 100 |

The composition applied to skin exhibiting pigmentation spots makes it possible to fade out the spots after several applications.

The invention claimed is:

1. A process for depigmenting and/or lightening skin exhibiting pigmentation spots and/or browned skin, the process comprising applying to the skin of a human in need thereof a composition comprising, in a physiologically acceptable medium:

at least one agent comprising a compound of formula (I),

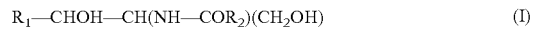

$$R_1\text{—CHOH—CH(NH—COR}_2)(\text{CH}_2\text{OH})\quad\text{(I)}$$

wherein $R_1$ denotes a $C_{11}$ to $C_{21}$ alkyl radical, and $R_2$ denotes a linear, $C_{11}$-$C_{19}$ hydrocarbon-based radical, and $R_2$ is optionally substituted with a hydroxyl group in an alpha-position with respect to the carbonyl, and optionally comprises one or more ethylenic groups; and at least one desquamating agent selected from the group consisting of salicylic acid, a salicylic acid derivative, and an aminosulphonic compound of formula (III),

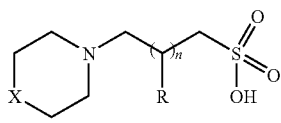
(III)

wherein
R denotes a hydrogen atom or an —OH group,
X denotes a N—CH$_2$CH$_2$OH group, and
n is equal to 0 or 1.

2. The process of claim 1, wherein the depigmenting is to eliminate brownish pigmentary spots, senescence spots, or both, and the lightening of the skin is for lightening browned skin.

3. The process of claim 1, wherein the composition comprises the compound of formula (I) in an amount ranging from 0.001% to 10% by weight, relative to the total weight of the composition.

4. The process of claim 1, wherein the composition further comprises at least one ingredient selected from the group of ingredients consisting of a calmative, an organic photoprotective agent and an inorganic photoprotective agent.

5. The process according to claim 1, wherein the at least one desquamating agent is a salicylic acid derivative selected from the group of compounds consisting of the compounds denoted by formula (II):

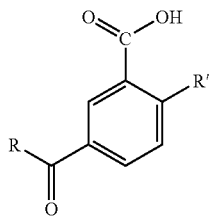
(II)

wherein:
R denotes an optionally substituted linear, branched or cyclic, saturated aliphatic chain comprising from 2 to 22 carbon atoms; an optionally substituted unsaturated chain comprising from 2 to 22 carbon atoms containing one or more optionally conjugated double bonds; an optionally substituted aromatic ring linked to the carbonyl radical directly or by saturated or unsaturated aliphatic chains comprising from 2 to 7 carbon atoms; and an optional substituent is at least one substituent optionally identical or different, selected from the group of substituents consisting of a halogen atom, a trifluoromethyl group, a hydroxyl group in free form, a hydroxyl group in a form esterified with an acid comprising from 1 to 6 carbon atoms, a carboxyl function in free form, and a carboxyl function in a form esterified with a lower alcohol comprising from 1 to 6 carbon atoms; and R' is a hydroxyl group, and a salt thereof derived from an inorganic or organic base.

6. The process of claim 5, wherein the radical R denotes an optionally substituted linear, branched or cyclic, saturated aliphatic chain comprising from 3 to 11 carbon atoms; or an optionally substituted unsaturated chain comprising from 3 to 17 carbon atoms and further comprising one or more optionally conjugated double bonds.

7. The process of claim 5, wherein the radical R is a $C_3$-$C_{11}$ alkyl group.

8. The process of claim 5, wherein the compound of formula (II) is selected from the group consisting of 5-n-octanoylsalicylic acid (or capryloylsalicylic acid), 5-n-decanoylsalicylic acid, 5-n-dodecanoylsalicylic acid, 5-n-heptyloxysalicylic acid, and a corresponding salt thereof.

9. The process of claim 8, wherein the compound of formula (II) is 5-n-octanoylsalicylic acid.

10. The process of claim 1, wherein the at least one desquamating agent is the aminosulfonic compound of formula (III) consisting of 4-(2-hydroxyethyl)piperazine-1-ethanesulphonic acid (HEPES).

* * * * *